United States Patent
Allen-Vercoe et al.

(10) Patent No.: US 11,098,377 B1
(45) Date of Patent: Aug. 24, 2021

(54) SYSTEMS AND METHODS FOR CHARACTERIZING COMPOSITIONS COMPRISING BACTERIAL POPULATIONS

(71) Applicant: NUBIYOTA LLC, Teaneck, NJ (US)

(72) Inventors: Emma Allen-Vercoe, Guelph (CA); Kyla Cochrane, Guelph (CA); Shawn Langer, Teaneck, NJ (US)

(73) Assignee: NUBIYOTA LLC, Teaneck, NJ (US)

( * ) Notice: Subject to any disclaimer, the term of this patent is extended or adjusted under 35 U.S.C. 154(b) by 0 days.

(21) Appl. No.: 17/021,528

(22) Filed: Sep. 15, 2020

(51) Int. Cl.
*C12Q 1/689* (2018.01)
*C12Q 1/04* (2006.01)
*C12N 15/10* (2006.01)

(52) U.S. Cl.
CPC ......... *C12Q 1/689* (2013.01); *C12N 15/1003* (2013.01); *C12Q 1/04* (2013.01)

(58) Field of Classification Search
CPC ....... C12Q 1/689; C12Q 1/04; C12N 15/1003
See application file for complete search history.

(56) References Cited

U.S. PATENT DOCUMENTS

| | | | | |
|---|---|---|---|---|
| 6,472,149 B1 * | 10/2002 | Gendre | ................. | C12Q 1/689 435/6.1 |
| 9,867,858 B2 * | 1/2018 | Borody | ................. | A61K 9/50 |
| 10,828,340 B2 * | 11/2020 | Jones | ................. | A61K 47/26 |
| 2004/0002126 A1 * | 1/2004 | Houde | ................. | G01N 33/569 435/7.32 |
| 2010/0136556 A1 * | 6/2010 | Friedberger | ................. | C12M 1/3446 435/6.16 |
| 2014/0342438 A1 * | 11/2014 | Allen-Vercoe | ................. | C12R 1/145 435/252.4 |
| 2014/0363397 A1 * | 12/2014 | Allen-Vercoe | ................. | A61K 35/74 424/93.3 |
| 2014/0363817 A1 * | 12/2014 | Dukan | ................. | G01N 33/582 435/6.11 |
| 2015/0374761 A1 * | 12/2015 | Sadowsky | ................. | A61K 35/741 424/489 |
| 2016/0289730 A1 * | 10/2016 | Pezacki | ................. | C12Q 1/10 |
| 2016/0331791 A1 * | 11/2016 | Borody | ................. | A61K 9/4858 |
| 2018/0250369 A1 * | 9/2018 | MacManus | ................. | A61P 29/00 |
| 2018/0251725 A1 * | 9/2018 | Allen-Vercoe | ................. | C12N 1/20 |
| 2019/0300843 A1 * | 10/2019 | Vongsa | ................. | A61K 35/741 |
| 2020/0078418 A1 * | 3/2020 | Wagner | ................. | A61K 35/741 |
| 2020/0147151 A1 * | 5/2020 | Dupont | ................. | A61K 35/742 |
| 2020/0254027 A1 * | 8/2020 | Dixit | ................. | A61K 47/18 |

FOREIGN PATENT DOCUMENTS

| | | | | |
|---|---|---|---|---|
| WO | WO-2013037067 A1 * | 3/2013 | ............... | A61P 29/00 |
| WO | WO-2017103225 A1 * | 6/2017 | ............... | A61P 1/10 |
| WO | WO-2018197951 A1 * | 11/2018 | ............... | A61K 47/10 |

OTHER PUBLICATIONS

Baxter et al.,Adverse events in faecal microbiota transplant: a review of the literature J. of Hospital Infection. 92 :117-127 (Year: 2016).*
Buffie et al., Precision microbiome reconstitution restores bile acid mediated resistance to Clostridium difficile. Nature 517 :205 (Year: 2015).*
Cammarota et al.,Fecal Microbiota Transplantation for the Treatment of Clostridium difficile Infection : Systematic Review J. of Clinical Gasteroenterology 48(8) : 693 (Year: 2014).*
Cao et al., Efficient utilization of complex N-linked glycans is a selective advantage for Bacteroides fragilis in extraintestinal infections. PNAS 111(35) :12901-12906 (Year: 2014).*
Costea et al., Towards standards for human fecal sample processing in metagenomic studies. Nature Biotechnology 35 (11) : 1069 (Year: 2017).*
Goldberg et al., Faecal microbiota transplantation for recurrent Clostridium difficile infection and beyond: risks andregulation. J. of Hospital Infection. 92 :115-116 (Year: 2016).*
Gough et al., Systematic Review of Intestinal Microbiota Transplantation (Fecal Bacteriotherapy) for Recurrent Clostridium difficile Infection. Clinical Infectious Diseases 53(10) :994 (Year: 2011).*
Gupta et al.,Fecal microbiota transplantation: in perspective. Therapeutic Advances in Gasterology 9(2) : 229-239 (Year: 2016).*
Heckly et al., A brief review of lyophilization damage and repair in bacterial preparations. Crtobiology 18 : 592-597 (Year: 1981).*
Heckly, R.J., Ch. 25 Principles of Preserving Bacteria by Freeze-Drying in Developments in Industrial Microbiology vol. 26 Publisher : Society for Industrial Microbiology (Year: 1984).*
Hellyer et alQuantitative Analysis of mRNA as a Marker for Viabilityof *Mycobacterium tuberculosis* . . . J. of Clinical Microbiology 37 (2) : 290 (Year: 1999).*
Hellyer etalDetection of Viable *Mycobacterium tuberculosis* by Reverse Transcriptase-Strand Displacement Amplification of mRNA. J. of Clinical Microbiology 37 (3) : 518 (Year: 1999).*
Keer et al.,Molecular methods for the assessment of bacterial viability. J. of Microbiological Methods 53 :175 (Year: 2003).*
Kelly et al.,Clinical Practice and Infrastructure Review of Fecal Microbiota Transplantation for Clostridium difficile Infection. Chest 153(1) : 266 (Year: 2018).*
Kulkarni et al., Unit 25B.10, Digital Multiplexed Gene Expression Analysis Using the NanoString nCounter System. Current Protocols in Molecular Biology 25B.10.1 (Year: 2011).*
Novick et al., Nucleic Acid and Protein Synthesis in Reconstituted Lyophilized *E. coli* Exposed to Air . J. of Applied Bacteriology 35 : 185 (Year: 1972).*

(Continued)

*Primary Examiner* — Ethan C Whisenant
(74) *Attorney, Agent, or Firm* — Greenberg Traurig, LLP

(57) ABSTRACT

A method includes reconstituting a lyophilized microbial community. Ribonucleic acid (RNA) is extracted from at least one targeted microbe in the reconstituted microbial community at a plurality of selected time periods. The RNA as extracted at the selected time period is subjected to a multiplex analyzer and determining RNA concentrations at the plurality of selected time periods. An increase in the RNA concentration from a first of the plurality of selected time periods to a second of the plurality of time periods indicates RNA expression from the at least one targeted microbe. RNA expression from the at least one targeted microbe indicates that the at least one targeted microbe is a living microbe.

18 Claims, 7 Drawing Sheets

(56) References Cited

OTHER PUBLICATIONS

Savini et al., Pilot-scale Production and Viability Analysis of Freeze-Dried Probiotic Bacteria Using Different Protective Agents. Nutrients 2 :330-339 (Year: 2010).*

Talmadge et al., Rapid immunologic reconstitution following transplantation with mobilized peripheral blood stem cells as compared to bone marrow. Bone Marrow Transplantation 19 : 161-172 (Year: 1997).*

Tang et al.Is frozen fecal microbiota transplantation as effective as fresh fecal microbiota transplantation in patients with recurrent or refractory Clostridium difficile infection: A meta-analysis? Diagnostic Microbiology and Infectious Disease 88 : 322-329 (Year: 2017).*

Taur et al.,Reconstitution of the gut microbiota of antibiotic-treated patients by autologous fecal microbiota transplant. Sci.Translational Medicine 10 : eaap9489 (Year: 2018).*

The Human Microbiome Project Consortium. Structure, function and diversity of the healthy human microbiome. Nature 486 : 207 (Year: 2012).*

Tian et al., Freeze-dried, Capsulized Fecal Microbiota Transplantation for Relapsing Clostridium difficile Infection. J. of Clinical Gasteroenterology 49(6) :537 (Year: 2015).*

\* cited by examiner

SYSTEMS AND METHODS FOR CHARACTERIZING COMPOSITIONS COMPRISING BACTERIAL POPULATIONS

FIELD OF THE TECHNOLOGY

At least some embodiments disclosed herein relate generally to therapies for treating gastrointestinal disorders. More particularly, at least some embodiments disclosed herein relate to systems and methods for identifying living reconstituted target microbes in bacterial populations used as therapies for treating disorders such as, but not limited to, gastrointestinal disorders, metabolic syndromes, psychological disorders (e.g., depression and anxiety), cancer, inflammatory disorders, autoimmune disorders, central nervous system disorders, and the like.

BACKGROUND

Compositions having bacterial populations such as fecal-derived bacterial populations can be used to treat disorders such as, but not limited to, gastrointestinal disorders. For example, Microbial Ecosystem Therapeutics (METs) can be used to treat gastrointestinal disorders and the like.

SUMMARY

In some embodiments, the method includes reconstituting a lyophilized microbial community. Ribonucleic acid (RNA) is extracted from at least one targeted microbe in the reconstituted microbial community at a plurality of selected time periods. The RNA as extracted is subjected at the selected time period to a multiplex analyzer and RNA concentrations at the plurality of selected time periods are determined. An increase in the RNA concentration from a first of the plurality of selected time periods to a second of the plurality of time periods indicates RNA expression from the at least one targeted microbe. RNA expression from the at least one targeted microbe indicates that the at least one targeted microbe is a living microbe.

In some embodiments, the method includes anaerobically reconstituting a first sample of a target microbe to produce a reconstituted target microbe and anaerobically reconstituting a community of microbes including a second sample of the target microbe to produce a reconstituted microbial community. Ribonucleic acid (RNA) is extracted from the reconstituted target microbe at a plurality of selected time periods after reconstitution and RNA is extracted from the reconstituted microbial community at the plurality of selected time periods after reconstitution. The RNA from the reconstituted target microbe is subjected at the plurality of selected time periods to a multiplex analyzer and determining RNA concentrations at the plurality of selected time periods and the RNA extracted from the reconstituted microbial community is subjected at the plurality of selected time periods to the multiplex analyzer and determining RNA concentrations at the plurality of selected time periods. The RNA concentration of the reconstituted target microbe is compared with the RNA concentration of the target microbe in the reconstituted microbial community. A lower RNA concentration of the reconstituted target microbe, relative to the RNA concentration of the target microbe in the reconstituted microbial community, indicates that the metabolic activity of the target microbe is enhanced by the community of microbes. A higher RNA concentration of the reconstituted target microbe, relative to the RNA concentration of the target microbe in the reconstituted microbial community, indicates that the metabolic activity of the target microbe is inhibited by the community of microbes.

In an embodiment, subjecting the RNA as extracted at the selected time period to the multiplex analyzer and determining RNA concentrations at the plurality of selected time periods includes detecting RNA without reverse transcription.

In an embodiment, subjecting the RNA as extracted at the selected time period to the multiplex analyzer and determining RNA concentrations at the plurality of selected time periods includes counting RNA without detecting complementary deoxyribonucleic acid (cDNA) as a proxy of the RNA.

In an embodiment, the multiplex analyzer is the nCounter® platform available from NanoString®.

In an embodiment, the microbial community includes bacteria strains included within a Microbial Ecosystem Therapeutic (MET). In an embodiment, the microbial community includes strains from MET-1, MET-2, MET-3, or MET-4.

In an embodiment, MET-1 includes *Acidaminococcus intestine; Bacteroides ovatus; Bifidobacterium adolescentis; Bifidobacterium longum; Blautia stercoris; Clostridium cocleatum; Collinsella aerofaciens; Dorea longicatena; Escherichia coli; Butyricicoccus pullicaecorum; Eubacterium eligens; Eubacterium limosum; Eubacterium rectale; Eubacterium ventriosum; Faecalibacterium prausnitzii; Lachnospira pectinoschiza; Lactobacillus casei; Lactobacillus paracasei; Parabacteroides distasonis; Enterobacter aerogenes; Roseburia faecis; Roseburia intestinalis; Ruminococcus obeum; Blautia luti; Ruminococcus torques*; and *Streptococcus mitis*.

In an embodiment, MET-2 includes *Parabacteroides merdae*; [*Eubacterium*] *hallii; Parabacteroides distasonis; Phascolarctobacterium succinatutens; Ruminococcus lactaris; Neglecta timonensis*; [*Clostridium*] *spiroforme; Roseburia intestinalis; Akkermansia muciniphila*; [*Ruminococcus*] *obeum*; [*Clostridium*] *lactatifermentans; Anaerovorax odorimutans*; [*Ruminococcus*] *torques; Eubacterium rectale; Bacteroides eggerthii; Roseburia inulinivorans*; [*Clostridium*] *hylemonae; Barnesiella intestinihominis*; [*Clostridium*] *aerotolerans; Bacteroides stercorirosoris; Flavonifractor plautii; Dorea longicatena; Blautia stercoris; Bifidobacterium longum; Coprococcus comes*; [*Eubacterium*] *eligens; Lactobacillus paracasei*; [*Clostridium*] *oroticum; Dorea formicigenerans; Escherichia coli; Anaerostipes hadrus; Blautia luti*; [*Clostridium*] *scindens; Eubacterium desmolans; Faecalibacterium prausnitzii; Bacteroides ovatus; Coprococcus catus; Bifidobacterium adolescentis; Collinsella aerofaciens*; and *Acidaminococcus intestine*.

In an embodiment, MET-3 includes *Parabacteroides merdae*; [*Eubacterium*] *hallii; Phascolarctobacterium succinatutens; Ruminococcus lactaris*; [*Clostridium*] *spiroforme; Roseburia intestinalis; Akkermansia muciniphila; Eubacterium rectale; Roseburia inulinivorans; Flavonifractor plautii; Dorea longicatena*; [*Eubacterium*] *eligens; Lactobacillus paracasei; Escherichia coli; Blautia luti*; [*Clostridium*] *scindens; Eubacterium desmolans; Faecalibacterium prausnitzii; Bacteroides ovatus; Coprococcus catus; Bifidobacterium adolescentis; Collinsella aerofaciens*; and *Acidaminococcus intestine*.

In an embodiment, MET-4 includes *Parabacteroides merdae*; [*Eubacterium*] *hallii; Parabacteroides distasonis; Phascolarctobacterium succinatutens; Akkermansia muciniphila; Anaerovorax odorimutans*; [*Ruminococcus*] *torques*; [*Eubacterium*] *rectale; Bacteroides eggerthii; Flavonifrac-* tor plautii; Dorea longicatena; Bifidobacterium longum; [Eubacterium] eligens; Lactobacillus paracasei; Anaerostipes hadrus; Blautia luti; [Clostridium] scindens; Eubacterium desmolans; Faecalibacterium prausnitzii; Coprococcus catus; Bifidobacterium adolescentis; Collinsella aerofaciens; Acidaminococcus intestine; Alistipes shahii; Bacteroides uniformis; [Clostridium] leptum; Enterococcus hirae; Gemmiger formicilis; Oscillibacter valericigenes; and Pseudoflavonifractor capillosus.

In an embodiment, the targeted microbe may initially decrease and then increase in gene expression.

In an embodiment, the targeted microbe may initially increase in gene expression.

In an embodiment, the targeted microbe may be one or more undesired pathogens. In such an embodiment, the absence of the targeted microbe can be used to validate that the one or more undesired pathogens are not present in the microbial community. In an embodiment, this can be used to establish a safety of the microbial community such as, for example, to establish to a regulatory agency such as the U.S. Food and Drug Administration (FDA) the safety of the microbial community for use in treating humans.

In an embodiment, a minimum increase in gene expression is at or about a 1.9 time increase from the first time period to the second time period. In an embodiment, a maximum increase in gene expression is at or about a 32.8 time increase from the first time period to the second time period. In an embodiment, a target increase in gene expression is at or about a 4.0 time increase from the first time period to the second time period.

BRIEF DESCRIPTION OF THE DRAWINGS

Reference is made to the drawings that form a part of this disclosure, and which illustrate embodiments in which the systems and methods described herein can be practiced.

Like reference numbers represent like parts throughout.

DETAILED DESCRIPTION

Figure 1:
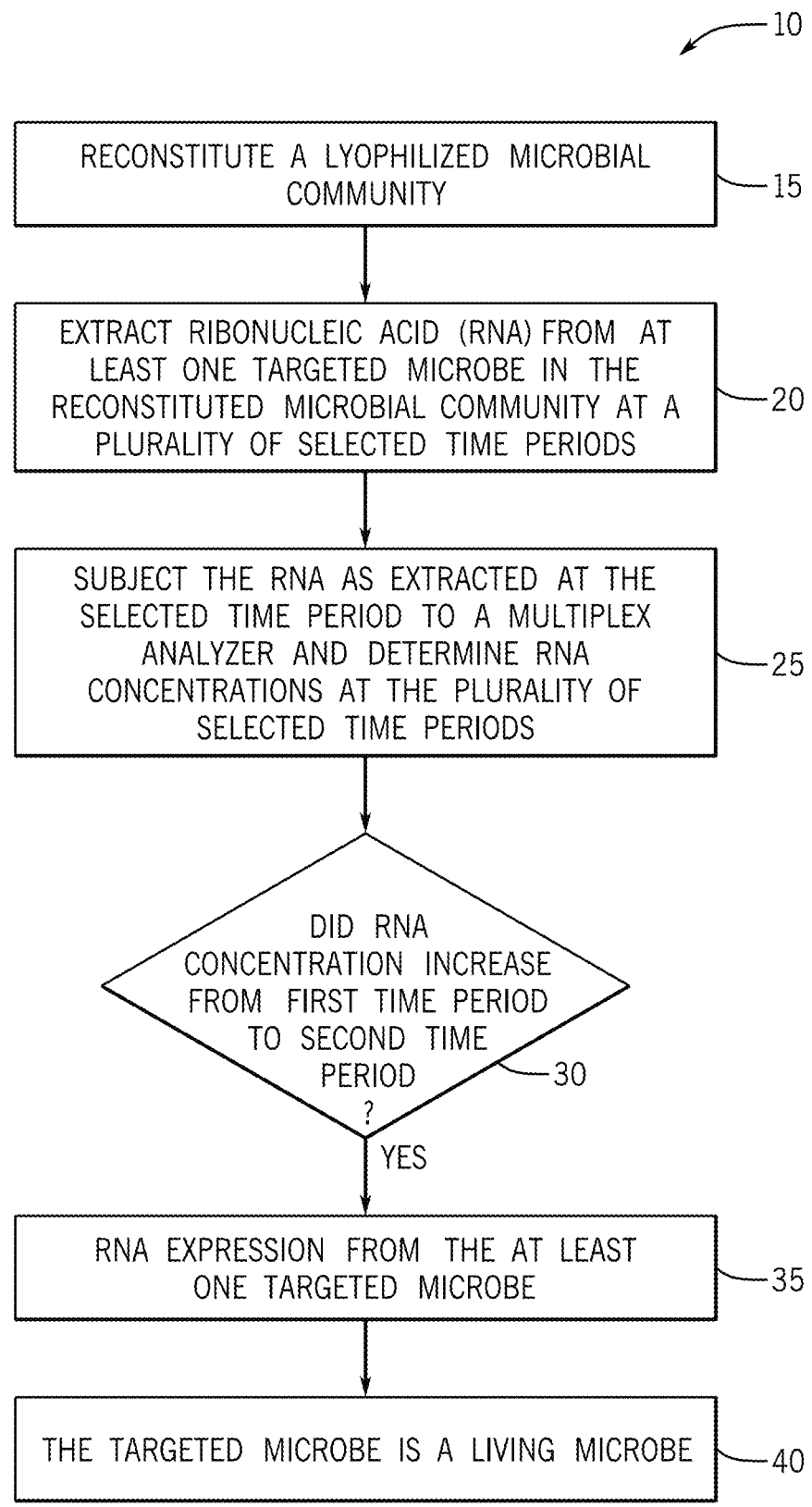
FIG. 1 shows a flowchart of a method, according to an embodiment.

Metabolic activity takes place in the cell of an organism. Metabolic activity includes sets of chemical reactions which are involved in maintaining the living state of the cell and are deemed essential for a living organism to maintain its life. Metabolic activity can be measured at the cellular level using the detection of increases (and/or decreases) in metabolic gene expression. These metabolically associated genes, or housekeeping genes, are constitutively expressed and therefore, are always on.

Measuring the changes in the expression of housekeeping genes, and more directly the increase in abundance of these genes, allows identification of whether microbes within a microbial community, such as, but not limited to, the microbes in a drug product, survive lyophilization and maintain metabolic processes.

In an embodiment, measuring the metabolic activity can rely upon measuring changes in housekeeping gene expression based on RNA count using a multiplex analyzer. The count values allow for easy analysis of the changes in metabolic gene expression over time. When the metabolic gene expression increases relative to a previous time point, the corresponding microbe is determined to be metabolizing.

In an embodiment, understanding the metabolic activity and the RNA expression can be used to assess whether a microbial community is effective for a patient. In an embodiment, in addition to assessing whether the microbial community is effective, the microbial community can be modified to tailor the microbial community in an MET to the patient to customize the patient's treatment. Similarly, the microbial community can be tailored to be more effective to particular disorders based on the RNA expression.

As used herein, the term "multiplex analyzer" refers to an apparatus capable of direct digital detection of messenger RNA (mRNA) molecules of interest using target specific, color-coded probe pairs. One example of a multiplex analyzer is the nCounter® Platform, commercially available from NanoString®. The nCounter® assay chemistry is based on hybridizing anti-sense capture and reporter probes to a ~100 base pair segment of the RNA target of interest. Each reporter probe carries a unique color-coded molecular barcode at the 5' end of the probe pair, which enables for the downstream detection of each target-probe complex via image acquisition and data processing using a digital analyzer. The capture probes all carry a biotin label at the 3' end that provides a molecular handle for attachment of the target-probe complex to the nCounter® cartridge, thereby immobilizing the complexes to allow for the removal of excess probes and the ability to ensure the correct orientation of the molecular barcodes from the 5' end. Hundreds of thousands of color codes designating mRNA targets of interest are directly imaged on the surface of the nCounter® cartridge using the digital analyzer. The expression level of a gene is measured by counting the number of times the color-coded barcode for that gene is detected, and the barcode counts are tabulated.

FIG. 1 shows a flowchart of a method 10, according to an embodiment. The method 10 can generally be performed to determine whether a targeted microbe within a microbial community is a living microbe.

The method 10 includes block 15 reconstituting a lyophilized microbial community. In an embodiment, block 15 can include, in an anaerobic chamber, re-suspending an amount of the lyophilized bacterial culture into a degassed anaerobic culture medium in a tube. For example, the amount subjected to resuspension can be two capsules (or 0.6 grams of the lyophilized bacterial culture). The anaerobic culture medium can be agar. The tube can be a conical centrifuge tube. The resuspension is allowed to fully reconstitute by rotating on a rotator for a selected time period such as up to 3 hours in an embodiment, or between and including 10 minutes and 2 hours in an embodiment (e.g., 10 minutes, 20 minutes, 30 minutes, 1 hour, 2 hours, etc.) minutes. A portion of the resuspension is anaerobically aliquoted into a RNAse free microcentrifuge tube. This can be repeated for each sample, as needed. The prepared aliquots are centrifuged at, for example, 12,000×g for 5 minutes at 4° C. In an embodiment, the prepared aliquots can be centrifuged at 10,000-14,000×g for 2-5 minutes at 4-8° C. The samples are then removed from the centrifuge and the supernatant decanted from each.

In an embodiment, prior to block 15, the method 10 can include lyophilizing the microbial community prior to reconstituting the lyophilized microbial community. In an embodiment, the lyophilizing can include, for example, the following method. Provide a primary culture of a microbial community. Transfer a portion of the primary culture equally divided into a plurality of centrifuge pots. The centrifuge pots are centrifuged for a selected centrifuging tim. An example centrifuging time is 10 minutes. In an embodiment, the centrifuge pots can be centrifuged for 8-12 minutes. The supernatant is decanted (as waste) and the full pellet in each centrifuge pot is retained. A portion of cryopreservation/lyopreservation medium is transferred into each centrifuge pot and each pellet is manually resuspended and homogenized. The centrifuge pot resuspensions are combined into a single centrifuge pot and manually homogenized. A portion of the combined resuspension is aliquoted into flasks until all the resuspension is transferred from the centrifuge pot. The flasks are stored at a temperature of at or about −80° C. for a selected storage time at least 24 hours. The lyophilizer is prepared to at least −65° C. The frozen cultures in the flasks are loaded into the lyophilizer. A lyophilization cycle is run including a primary drying cycle of at least 33 hours. After the lyophilization cycle, physical characteristics are evaluated to ensure they are adequate.

At block 20 the method 10 includes extracting ribonucleic acid (RNA) from at least one targeted microbe in the reconstituted microbial community at a plurality of selected time periods. In an embodiment, the plurality of selected time periods is up to at or about 2 hours after reconstitution. It is to be appreciated that the plurality of selected time periods can extend beyond 2 hours, though some of the microbes may start dying off in durations beyond 2 hours. In an embodiment, the plurality of selected time periods is up to at or about 1 hour after reconstitution. In an embodiment, the selected time periods are, but are not limited to, 0 minutes, 10 minutes, 30 minutes, 1 hour, and 2 hours after reconstitution. It is to be appreciated that these numbers are examples and can include one or more time periods that vary beyond the stated time periods (e.g., 20 minutes, 40 minutes, or the like).

In an embodiment, block 20 can include resuspending a sample in a solution including chelating agents, detergent, and a buffer (e.g., the Max Bacterial Enhancement Reagent commercially available from Thermo Fisher Scientific) that has been heated to, for example, 95° C. using a dry water bath. In an embodiment, the temperature can be from 90-100° C. The tube(s) is/are incubated. Incubation can be at a temperature of at or about 95° C. for at or about 4 minutes. A pretreatment (e.g., TRIzol™ commercially available from Thermo Fisher Scientific) for the solution including chelating agents, detergent, and a buffer added to the lysate and mixed. The tube(s) are incubated at room temperature for at or about 5 minutes. An equal volume of a non-polar organic solvent (e.g., a suitable alcohol) is added to a sample lysed in the pretreatment and mixed thoroughly. For example, the non-polar organic solvent is ethanol (95%-100%). The mixture is transferred to a collection tube and centrifuged at 10,000×g for 1 minute. An RNA wash buffer is added to the collection tube and centrifuged at 10,000×g for 1 minute. In an RNAse free tube, a nuclease such as DNase I and DNA Digestion Buffer is added. The mix is added directly to the matrix which is incubated at room temperature for 15 minutes. A prewash (e.g., the Direct-zol RNA PreWash commercially available from Zymo Research) is added and centrifuged at 10,000×g for 1 minute. Flow-through is discarded and the prewash and centrifuging is repeated. An RNA wash buffer is added and centrifuged at 10,000×g for 2 minutes. The column is transferred carefully to an RNAse free microtube. To elute RNA, DNase/RNAse free water is added directly to the column matrix and centrifuged at 10,000×g for 1 minute.

Figure 4A:
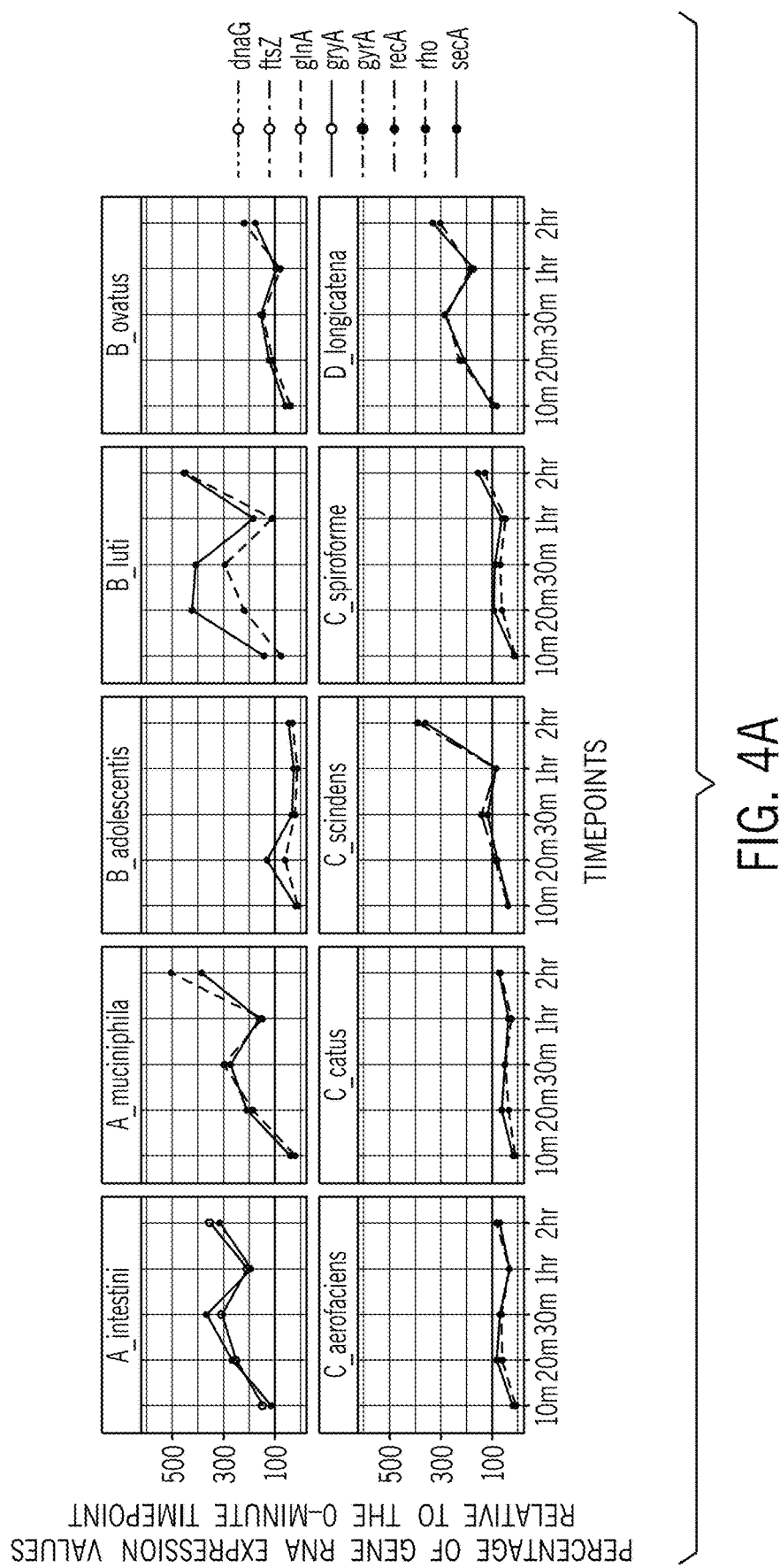
FIGS. 4A-4B show percentage changes of RNA expression values relative to a 0-minute timepoint for different microbes and for a plurality of probes for each microbe, according to an embodiment.
Figure 4B:
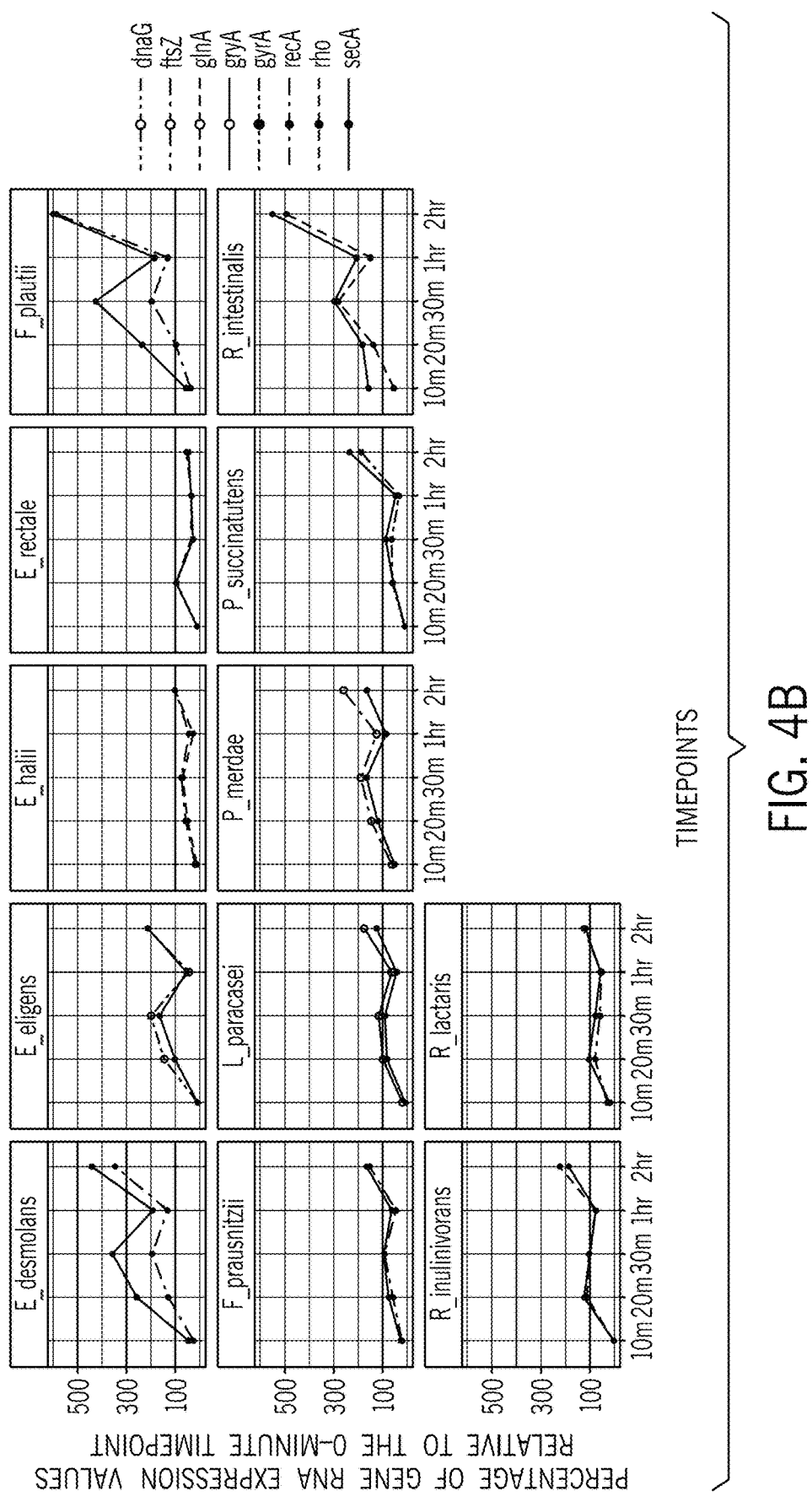

At block 25 the method 10 includes subjecting the RNA as extracted at the selected time period to a multiplex analyzer and determining RNA concentrations at the plurality of selected time periods. For example, in an embodiment, the RNA as extracted at 0 minutes after reconstitution and at 10 minutes after reconstitution is submitted to the multiplex analyzer to determine the RNA concentrations at 0 minutes and at 10 minutes for the targeted microbe. FIGS. 4A-4B show percentage changes of RNA expression values relative to the 0-minute timepoint at 0 minutes, 10 minutes, 20 minutes, 30 minutes, 1 hour, and 2 hours after reconstitution. In an embodiment, the RNA as extracted includes a sample of at least 100 ng. In an embodiment, the RNA as extracted may be a sample that is smaller than 100 ng, though at least 100 ng may be preferred. In an embodiment, the multiplex analyzer directly counts RNA without reverse transcription. As a result, the RNA is counted without detecting complementary deoxyribonucleic acid (cDNA) as a proxy of the RNA.

At block 30, if an increase in the RNA concentration from a first of the plurality of selected time periods to a second of the plurality of time periods is determined, then there has been RNA expression from the at least one targeted microbe. In an embodiment, a minimum increase in gene expression is at or about a 1.9 time increase from the first time period to the second time period. In an embodiment, a maximum increase in gene expression is at or about a 32.8 time increase from the first time period to the second time period. In an embodiment, a target increase in gene expression is at or about a 4.0 time increase from the first time period to the second time period. It is to be appreciated that these numbers are examples and can vary beyond the stated values. For example, so long as an increase in gene expression is greater than 1×, then gene expression has changed. Similarly, there may be no maximum increase in gene expression and it can be larger than 32.8×.

At block 35, if an increase in the RNA concentration from a first of the plurality of selected time periods to a second of the plurality of selected time periods is determined, then RNA expression from the at least one targeted microbe occurred and indicates that the at least one targeted microbe is a living microbe (block 40). This is because, for example, if the at least one targeted microbe is not a living microbe, then the RNA expression would not increase over time after reconstitution. In FIGS. 4A-4B, some declines in the RNA expression are identified. This is expected due to a degradation of the RNA during the lyophilization process. However, because the RNA as extracted is subjected to analysis at a plurality of selected time periods, it is observed that the RNA expression recovers from the initial degradation and RNA expression increases over time. This is also shown in FIGS. 4A-4B.

In an embodiment, the targeted microbe may be one or more undesired pathogens. In such an embodiment, the absence of the targeted microbe can be used to validate that the one or more undesired pathogens are not present in the microbial community. In an embodiment, this can be used to establish a safety of the microbial community such as, for example, to establish to a regulatory agency such as the U.S.

Food and Drug Administration (FDA) the safety of the microbial community for use in treating humans.

In an embodiment, it may be possible to compare results of the method 10 with a similar microbial analysis of a patient's fecal matter to confirm that an MET is working as expected within the patient. Additionally, it may be possible to use the method 10 to tailor a specific MET to a particular patient based on a test of the patient's fecal matter. An embodiment of a method for treating a patient is disclosed in accordance with FIG. 6 below.

Figure 2:
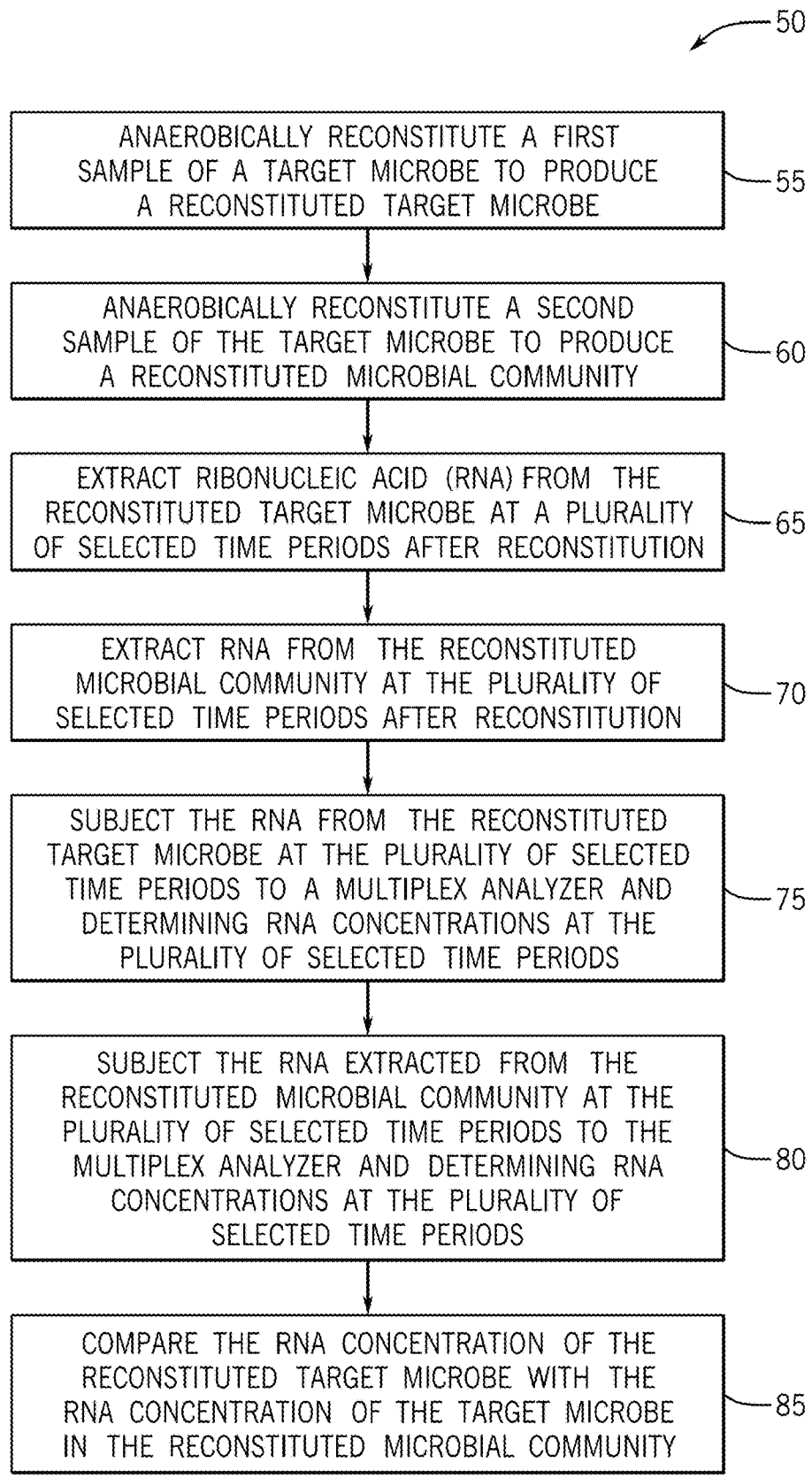
FIG. 2 shows a flowchart of a method, according to an embodiment.

FIG. 2 shows a flowchart of a method 50, according to an embodiment. The method 50 can generally be performed to determine whether a targeted microbe within a community of microbes is a living microbe. The method 50 includes similar aspects to those from the method 10 in FIG. 1 above. The method 50 additionally includes a comparison between the targeted microbe outside of a microbial community and the targeted microbe within a microbial community to characterize the impact of the targeted microbe being disposed within a microbial community instead of merely as a single microbe. This can, for example, be advantageous in crafting a microbial community for treatment of certain disorders, such as, but not limited to, gastrointestinal disorders.

The method 50 includes block 55 anaerobically reconstituting a first sample of a target microbe to produce a reconstituted target microbe. In an embodiment, block 55 can include, in an anaerobic chamber, re-suspending an amount of the lyophilized bacterial culture into a degassed anaerobic culture medium in a tube. For example, the amount subjected to resuspension can be two capsules (or 0.6 grams of the lyophilized bacterial culture). The anaerobic culture medium can be agar. The tube can be a conical centrifuge tube. The resuspension is allowed to fully reconstitute by rotating on a rotator for a selected time period such as up to 3 hours in an embodiment, or between and including 10 minutes and 2 hours in an embodiment (e.g., 10 minutes, 20 minutes, 30 minutes, 1 hour, 2 hours, etc.) minutes. A portion of the resuspension is anaerobically aliquoted into a RNAse free microcentrifuge tube. This can be repeated for each sample, as needed. The prepared aliquots are centrifuged at, for example, 12,000×g for 5 minutes at 4° C. In an embodiment, the prepared aliquots can be centrifuged at 10,000-14,000×g for 2-5 minutes at 4-8° C. The samples are then removed from the centrifuge and the supernatant decanted from each.

In an embodiment, the method 50 can include lyophilizing the first sample of the target microbe prior to the reconstituting at block 55. In an embodiment, the lyophilizing can include, for example, the following method. Provide a primary culture of a microbial community. Transfer a portion of the primary culture equally divided into a plurality of centrifuge pots. The centrifuge pots are centrifuged for a selected centrifuging time. An example centrifuging time is 10 minutes. In an embodiment, the centrifuge pots can be centrifuged for 8-12 minutes. The supernatant is decanted (as waste) and the full pellet in each centrifuge pot is retained. A portion of cryopreservation/lyopreservation medium is transferred into each centrifuge pot and each pellet is manually resuspended and homogenized. The centrifuge pot resuspensions are combined into a single centrifuge pot and manually homogenized. A portion of the combined resuspension is aliquoted into flasks until all the resuspension is transferred from the centrifuge pot. The flasks are stored at a temperature of at or about −80° C. for a selected storage time at least 24 hours. The lyophilizer is prepared to at least −65° C. The frozen cultures in the flasks are loaded into the lyophilizer. A lyophilization cycle is run including a primary drying cycle of at least 33 hours. After the lyophilization cycle, physical characteristics are evaluated to ensure they are adequate.

At block 60, a community of microbes including a second sample of the target microbe are anaerobically reconstituted to produce a reconstituted microbial community. In an embodiment, block 60 can include, in an anaerobic chamber, re-suspending an amount of the lyophilized bacterial culture into a degassed anaerobic culture medium in a tube. For example, the amount subjected to resuspension can be two capsules (or 0.6 grams of the lyophilized bacterial culture). The anaerobic culture medium can be agar. The tube can be a conical centrifuge tube. The resuspension is allowed to fully reconstitute by rotating on a rotator for a selected time period such as up to 3 hours in an embodiment, or between and including 10 minutes and 2 hours in an embodiment (e.g., 10 minutes, 20 minutes, 30 minutes, 1 hour, 2 hours, etc.) minutes. A portion of the resuspension is anaerobically aliquoted into a RNAse free microcentrifuge tube. This can be repeated for each sample, as needed. The prepared aliquots are centrifuged at, for example, 12,000×g for 5 minutes at 4° C. In an embodiment, the prepared aliquots can be centrifuged at 10,000-14,000×g for 2-5 minutes at 4-8° C. The samples are then removed from the centrifuge and the supernatant decanted from each.

In an embodiment, the method 50 includes lyophilizing the microbial community including the second sample of the target microbe prior to the reconstituting at block 60. In an embodiment, the lyophilizing can include, for example, the following method. Provide a primary culture of a microbial community. Transfer a portion of the primary culture equally divided into a plurality of centrifuge pots. The centrifuge pots are centrifuged for a selected centrifuging time. An example centrifuging time is 10 minutes. In an embodiment, the centrifuge pots can be centrifuged for 8-12 minutes. The supernatant is decanted (as waste) and the full pellet in each centrifuge pot is retained. A portion of cryopreservation/lyopreservation medium is transferred into each centrifuge pot and each pellet is manually resuspended and homogenized. The centrifuge pot resuspensions are combined into a single centrifuge pot and manually homogenized. A portion of the combined resuspension is aliquoted into flasks until all the resuspension is transferred from the centrifuge pot. The flasks are stored at a temperature of at or about −80° C. for a selected storage time at least 24 hours. The lyophilizer is prepared to at least −65° C. The frozen cultures in the flasks are loaded into the lyophilizer. A lyophilization cycle is run including a primary drying cycle of at least 33 hours. After the lyophilization cycle, physical characteristics are evaluated to ensure they are adequate.

At block 65 the method 50 includes extracting ribonucleic acid (RNA) from the reconstituted target microbe at a plurality of selected time periods after reconstitution. In an embodiment, the plurality of selected time periods is up to at or about 2 hours after reconstitution. In an embodiment, the plurality of selected time periods is up to at or about 1 hour after reconstitution. In an embodiment, the selected time periods are, but are not limited to, 0 minutes, 10 minutes, 30 minutes, 1 hour, and 2 hours after reconstitution. It is to be appreciated that these numbers are examples and can include one or more time periods that vary beyond the stated time periods (e.g., 20 minutes, 40 minutes, or the like). It is to be appreciated that the plurality of selected time periods can extend beyond 2 hours, though some of the microbes may start dying off in durations beyond 2 hours.

In an embodiment, block 65 can include resuspending a sample in a solution including chelating agents, detergent, and a buffer (e.g., the Max Bacterial Enhancement Reagent commercially available from Thermo Fisher Scientific) that has been heated to, for example, 95° C. using a dry water bath. In an embodiment, the temperature can be from 90-100° C. The tube(s) is/are incubated. Incubation can be at a temperature of at or about 95° C. for at or about 4 minutes. A pretreatment (e.g., TRIzol™ commercially available from Thermo Fisher Scientific) for the solution including chelating agents, detergent, and a buffer added to the lysate and mixed. The tube(s) are incubated at room temperature for at or about 5 minutes. An equal volume of a non-polar organic solvent (e.g., a suitable alcohol) is added to a sample lysed in the pretreatment and mixed thoroughly. For example, the non-polar organic solvent is ethanol (95%-100%). The mixture is transferred to a collection tube and centrifuged at 10,000×g for 1 minute. An RNA wash buffer is added to the collection tube and centrifuged at 10,000×g for 1 minute. In an RNAse free tube, a nuclease such as DNase I and DNA Digestion Buffer is added. The mix is added directly to the matrix which is incubated at room temperature for 15 minutes. A prewash (e.g., the Direct-zol RNA PreWash commercially available from Zymo Research) is added and centrifuged at 10,000×g for 1 minute. Flow-through is discarded and the prewash and centrifuging is repeated. An RNA wash buffer is added and centrifuged at 10,000×g for 2 minutes. The column is transferred carefully to an RNAse free microtube. To elute RNA, DNase/RNAse free water is added directly to the column matrix and centrifuged at 10,000×g for 1 minute.

At block 70 the method 50 includes extracting RNA from the reconstituted microbial community at the plurality of selected time periods after reconstitution. The plurality of selected time periods at block 70 are the same as the plurality of selected time periods at block 65. That is, the plurality of selected time periods are up to at or about 2 hours after reconstitution. In an embodiment, the plurality of selected time periods are up to at or about 1 hour after reconstitution. In an embodiment, the selected time periods are, but are not limited to, 0 minutes, 10 minutes, 30 minutes, 1 hour, and 2 hours after reconstitution. It is to be appreciated that these numbers are examples and can include one or more time periods that vary beyond the stated time periods (e.g., 20 minutes, 40 minutes, or the like). In an embodiment, the RNA as extracted may be a sample that is smaller than 100 ng, though at least 100 ng may be preferred.

In an embodiment, block 70 can include resuspending a sample in a solution including chelating agents, detergent, and a buffer (e.g., the Max Bacterial Enhancement Reagent commercially available from Thermo Fisher Scientific) that has been heated to, for example, 95° C. using a dry water bath. In an embodiment, the temperature can be from 90-100° C. The tube(s) is/are incubated. Incubation can be at a temperature of at or about 95° C. for at or about 4 minutes. A pretreatment (e.g., TRIzol™ commercially available from Thermo Fisher Scientific) for the solution including chelating agents, detergent, and a buffer added to the lysate and mixed. The tube(s) are incubated at room temperature for at or about 5 minutes. An equal volume of a non-polar organic solvent (e.g., a suitable alcohol) is added to a sample lysed in the pretreatment and mixed thoroughly. For example, the non-polar organic solvent is ethanol (95%-100%). The mixture is transferred to a collection tube and centrifuged at 10,000×g for 1 minute. An RNA wash buffer is added to the collection tube and centrifuged at 10,000×g for 1 minute. In an RNAse free tube, a nuclease such as DNase I and DNA Digestion Buffer is added. The mix is added directly to the matrix which is incubated at room temperature for 15 minutes. A prewash (e.g., the Direct-zol RNA PreWash commercially available from Zymo Research) is added and centrifuged at 10,000×g for 1 minute. Flow-through is discarded and the prewash and centrifuging is repeated. An RNA wash buffer is added and centrifuged at 10,000×g for 2 minutes. The column is transferred carefully to an RNAse free microtube. To elute RNA, DNase/RNAse free water is added directly to the column matrix and centrifuged at 10,000×g for 1 minute.

At block 75 the method 50 includes subjecting the RNA from the reconstituted target microbe at the plurality of selected time periods to a multiplex analyzer and determining RNA concentrations at the plurality of selected time periods. For example, in an embodiment, the RNA as extracted at 0 minutes after reconstitution and at 10 minutes after reconstitution is submitted to the multiplex analyzer to determine the RNA concentrations at 0 minutes and at 10 minutes for the targeted microbe. FIGS. 4A-4B show percentage changes of RNA expression values relative to the 0-minute timepoint at 0 minutes, 10 minutes, 20 minutes, 30 minutes, 1 hour, and 2 hours after reconstitution. In an embodiment, the RNA as extracted includes a sample of at least 100 ng. In an embodiment, the RNA as extracted may be a sample that is smaller than 100 ng, though at least 100 ng may be preferred. In an embodiment, the multiplex analyzer directly counts RNA without reverse transcription. As a result, the RNA is counted without detecting complementary deoxyribonucleic acid (cDNA) as a proxy of the RNA.

At block 80 the method 50 includes subjecting the RNA extracted from the reconstituted microbial community at the plurality of selected time periods to the multiplex analyzer and determining RNA concentrations at the plurality of selected time periods. Similar to block 70, the plurality of selected time periods at block 80 match the plurality of selected time periods at block 75. Thus, in an embodiment, the RNA as extracted at 0 minutes after reconstitution and at 10 minutes after reconstitution are submitted to the multiplex analyzer to determine the RNA concentrations at 0 minutes and at 10 minutes for the targeted microbe. FIGS. 4A-4B show percentage changes of RNA expression values relative to the 0-minute timepoint at 0 minutes, 10 minutes, 20 minutes, 30 minutes, 1 hour, and 2 hours after reconstitution. In an embodiment, the multiplex analyzer directly counts RNA without reverse transcription. As a result, the RNA is counted without detecting complementary deoxyribonucleic acid (cDNA) as a proxy of the RNA.

At block 85 the method 50 includes comparing the RNA concentration of the reconstituted target microbe with the RNA concentration of the target microbe in the reconstituted microbial community. A lower RNA concentration of the reconstituted target microbe, relative to the RNA concentration of the target microbe in the reconstituted microbial community, indicates that the metabolic activity of the target microbe is enhanced by the community of microbes. A higher RNA concentration of the reconstituted target microbe, relative to the RNA concentration of the target microbe in the reconstituted microbial community, indicates that the metabolic activity of the target microbe is inhibited by the community of microbes. In an embodiment, a minimum increase in gene expression is at or about a 1.9 time increase from the first time period to the second time period. In an embodiment, a maximum increase in gene expression is at or about a 32.8 time increase from the first time period to the second time period. In an embodiment, a target increase in gene expression is at or about a 4.0 time increase from the first time period to the second time period. It is to be appreciated that these numbers are examples and can vary beyond the stated values. For example, so long as an increase in gene expression is greater than 1×, then gene expression has changed. Similarly, there may be no maximum increase in gene expression and it can be larger than 32.8×.

In an embodiment, the method 50 can be used to design a community of microbes that will provide more effective treatments for disorders (e.g., gastrointestinal disorders) than a single microbe on its own. The method 50 can also be used to assess the efficacy of the microbial community and determine negative interactions between the microbes within the community of microbes.

In an embodiment, the targeted microbe may be one or more undesired pathogens. In such an embodiment, the absence of the targeted microbe can be used to validate that the one or more undesired pathogens are not present in the microbial community. In an embodiment, this can be used to establish a safety of the microbial community such as, for example, to establish to a regulatory agency such as the U.S. Food and Drug Administration (FDA) the safety of the microbial community for use in treating humans.

In an embodiment, it may be possible to compare results of the method 50 with a similar microbial analysis of a patient's fecal matter to confirm that an MET is working as expected within the patient. Additionally, it may be possible to use the method 50 to tailor a specific MET to a particular patient based on a test of the patient's fecal matter.

Figure 3:
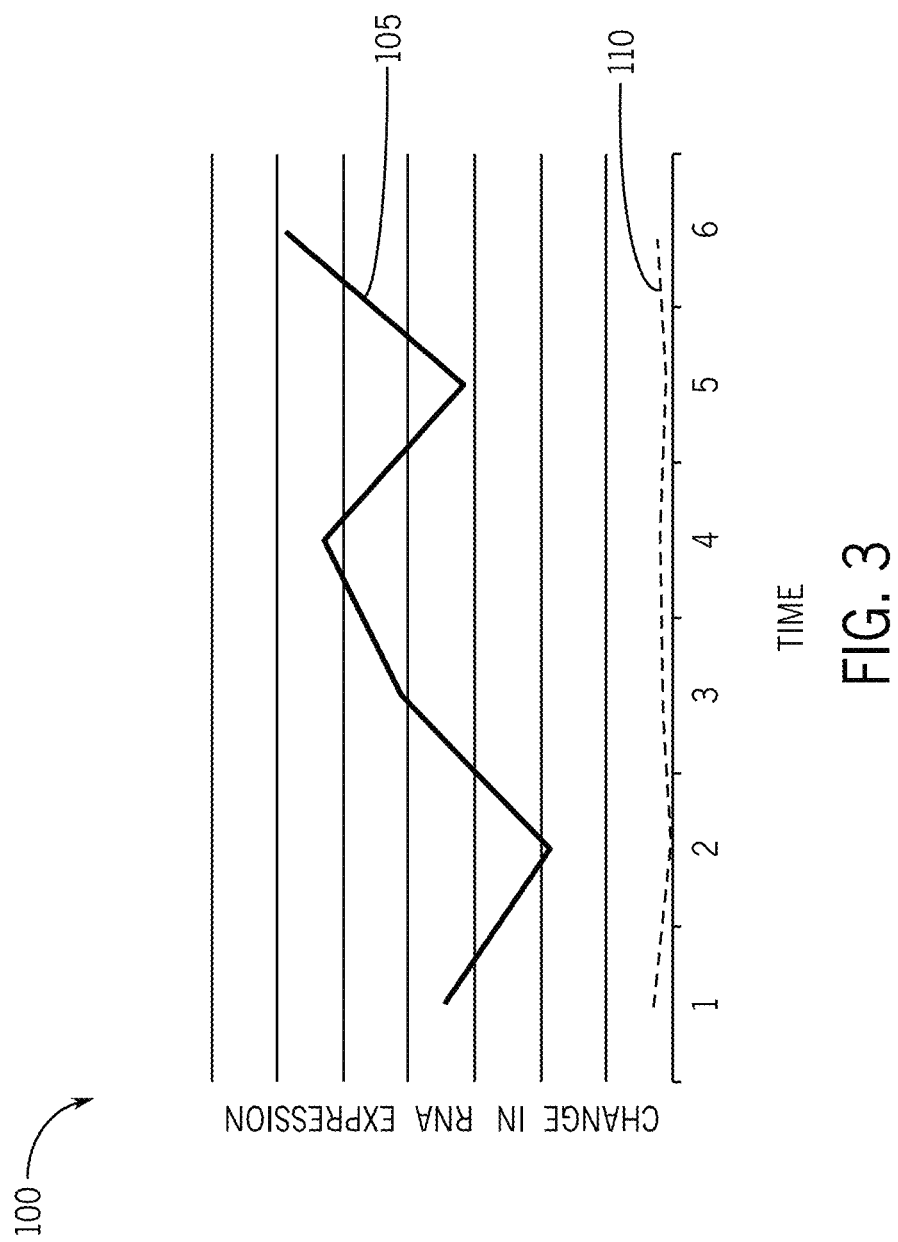
FIG. 3 is a chart that shows RNA expression over time for a microbe within a microbial community, according to an embodiment.

FIG. 3 is a chart 100 that shows RNA expression over time for a microbe within a microbial community, according to an embodiment. In the chart 100, the x-axis represents a plurality of selected time periods 1-6. The plurality of selected time periods 1-6 appear to be the same size, but it is to be appreciated that the duration of the time periods is not intended to be limited. In an embodiment, the time periods 1-6 can correspond to time periods within the selected time periods used in the methods 10 and 50 described in accordance with FIGS. 1 and 2 above. As is generally shown, the reconstituted microbe generally has a velocity of change of RNA expression that shows whether the targeted microbe is thriving or struggling within the microbial community. For example, a first target microbe 105 includes steeper increases in RNA expression relative to a second target microbe 110. This can, for example, indicate that the second target microbe is not interacting well within the microbial community and is thus struggling to express RNA. In the illustrated embodiment, the first targeted microbe 105 and the second targeted microbe 110 both exhibit a decline in RNA expression from time 1 to time 2. This decline may generally occur because, for example, some of the RNA degrades when the microbial community is lyophilized. If the targeted microbes survive the lyophilization process, then as shown in FIG. 3, the RNA expression will begin to increase after time 2. It is to be appreciated that the RNA does not always degrade to the point that the RNA expression declines from time 1 to time 2. This is illustrated in Example 1 below and corresponding FIGS. 4A-4B. Although not shown in FIG. 3, when a threshold value is achieved and maintained in the RNA expression, then the microbial community can be considered to be stable. In an embodiment, the threshold value can be selected to be when expression exceeds degradation. In an embodiment, the targeted microbes can be tailored to "wake up" at different time periods. That is, in an embodiment, the first target microbe 105 can intentionally begin increasing in RNA expression at an earlier time than the second target microbe 110. This can be based on, for example, the treatment or disorder being treated, the patient being treated, the microbes within the community, or the like.

Example 1

FIGS. 4A and 4B show a plurality of charts prepared based on RNA expression according to the method 50 above. Additionally, when the charts for the different probes align for a single target microbe, the community of microbes may be considered stable. As illustrated, the target microbes within MET-3 (as defined above) were tested according to method 50, and the resulting percentage changes of RNA expression values relative to the 0-minute timepoint are detailed in FIGS. 4A-4B. There are two manners of RNA expression shown in the test results. For some of the target microbes, there is an initial drop in RNA expression (e.g., <100% relative to 0-minute timepoint). This can be identified as being a result of the degradation of RNA that occurs due to lyophilization or, in some cases, as a result of the interaction with the community of microbes. For the other target microbes, RNA expression increases without any decrease (e.g., >100% relative to the 0-minute timepoint).

Figure 5:
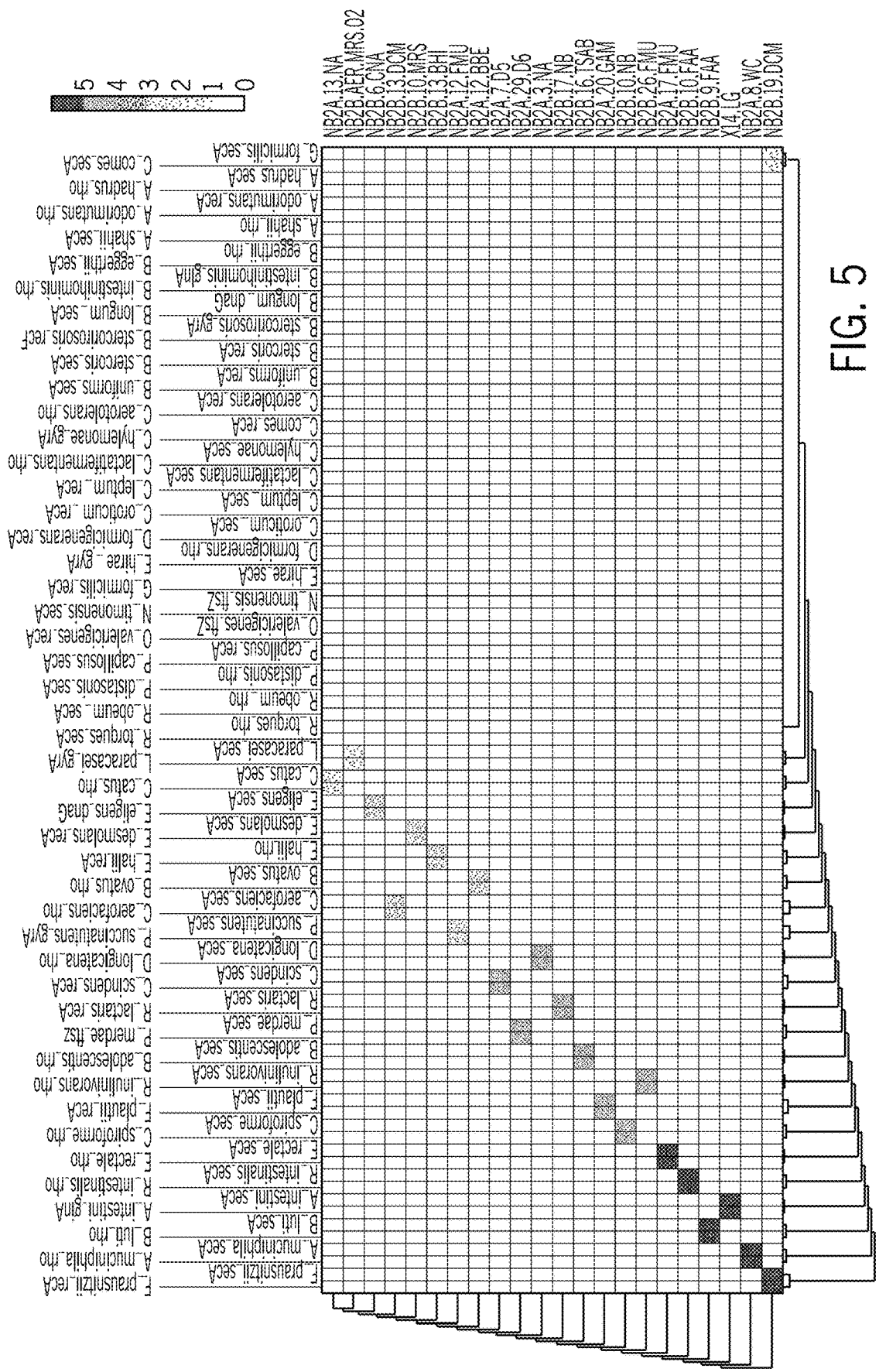
FIG. 5 shows a heat map identifying target microbes within a microbial community that were identified using the method of FIG. 2, according to an embodiment.

FIG. 5 shows a heat map identifying target microbes within a microbial community that were identified using the method of FIG. 2, according to an embodiment. FIG. 5 shows that even when a microbial community includes a plurality of microbes that are not being targeted, the method of FIG. 2 can be used to identify only the targeted microbes within the community. Such targeted microbes are highlighted in the figure, while the remaining microbes are not highlighted.

Figure 6:
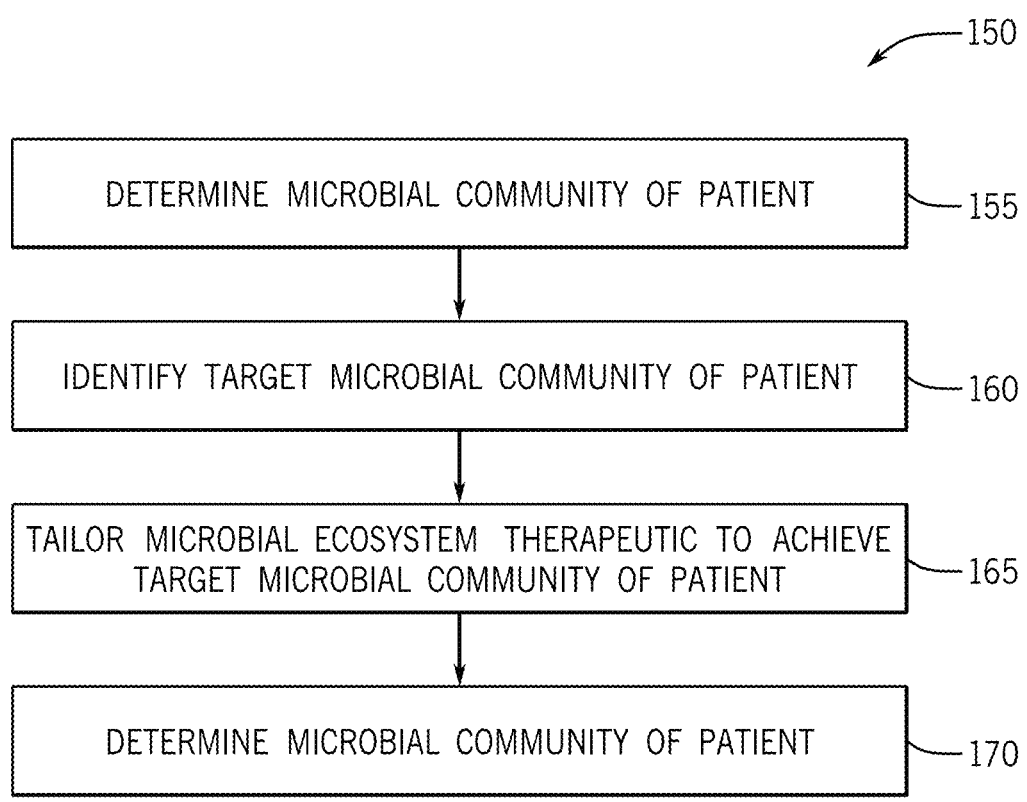
FIG. 6 shows a flowchart of a method for treatment using a microbial community, according to an embodiment.

FIG. 6 shows a flowchart of a method 150 for treatment using a microbial community, according to an embodiment.

At block 155, the method 150 includes determining a microbial community of a patient. In an embodiment, this includes, for example, analyzing the fecal matter of the patient to identify which gut bacteria is present and/or may be missing from the patient.

At block 160, the method 150 includes identifying a target microbial community of the patient based on the determined microbial community. For example, if the patient lacks a particular microbe, has too much of a particular microbe, or the like, then the target microbial community can be crafted to achieve the targeted microbial community.

At block 165, the method 150 includes tailoring a Microbial Ecosystem Therapeutic (MET) to achieve the target microbial community of the patient. At block 165, the method 50 (FIG. 1) and/or the method 100 (FIG. 2) can be used to prepare the microbial community based on the targeted needs. The target microbial community can be evaluated for potential efficacy and to confirm that the microbial community appears to have a chance of success in the patient.

At block 170, the method 150 can optionally include again determining the microbial community of the patient once the patient has taken the MET. As in block 155, block 170 includes analyzing the fecal matter of the patient. Block 170 can be representative of a validation step to confirm that the microbial community provided to the patient via the customized MET was effective in this patient. This can, for example, aid in customizing a treatment plan for a patient based on the actual interaction of the microbial community relative to the expected interaction of the microbial community. Alternatively, if at block 170, the microbial community does not appear to be successful in helping the patient, then blocks 160 and 165 can again be completed.

Aspects:

It is to be appreciated that any of aspects 1-13 can be combined with any of aspects 14-24, 28, 29, 32, 33, 35, or 36. Any of aspects 14-24 can be combined with any of aspects 28, 29, 32, 33, 35, or 36.

Aspect 1. A method, comprising: reconstituting a lyophilized microbial community; extracting ribonucleic acid (RNA) from at least one targeted microbe in the reconstituted microbial community at a plurality of selected time periods; subjecting the RNA as extracted at the selected time period to a multiplex analyzer and determining RNA concentrations at the plurality of selected time periods, wherein an increase in the RNA concentration from a first of the plurality of selected time periods to a second of the plurality of time periods indicates RNA expression from the at least one targeted microbe, and wherein RNA expression from the at least one targeted microbe indicates that the at least one targeted microbe is a living microbe.

Aspect 2. The method of aspect 1, wherein the plurality of selected time periods are between and including 0 minutes and 2 hours.

Aspect 3. The method of one of aspects 1 or 2, wherein the plurality of selected time periods include 0 minutes, 10 minutes, 30 minutes, and 1 hour after the at least one targeted microbe is reconstituted.

Aspect 4. The method of aspect 3, wherein an increase in RNA concentration is determined between and including 0 minutes and at least one of 10 minutes, 20 minutes, 30 minutes, 1 hour, or 2 hours.

Aspect 5. The method of any of aspects 1-4, comprising: lyophilizing the microbial community prior to the reconstituting.

Aspect 6. The method of any of aspect 1-5, comprising: freezing the microbial community.

Aspect 7. The method of any of aspects 1-6, wherein the multiplex analyzer includes a NanoString® RNA Assay.

Aspect 8. The method of any of aspects 1-7, wherein the reconstituting includes anaerobically reconstituting the lyophilized microbial community.

Aspect 9. The method of any of aspects 1-8, wherein the targeted microbe is a strain included in one or more of MET-1, MET-2, MET-3, or MET-4 as defined above.

Aspect 10. The method of any of aspects 1-9, wherein subjecting the RNA as extracted at the selected time period to the multiplex analyzer and determining RNA concentrations at the plurality of selected time periods includes detecting RNA without reverse transcription.

Aspect 11. The method of aspect 10, wherein subjecting the RNA as extracted at the selected time period to the multiplex analyzer and determining RNA concentrations at the plurality of selected time periods includes counting RNA without detecting complementary deoxyribonucleic acid (cDNA) as a proxy of the RNA.

Aspect 12. The method of aspect 10, wherein subjecting the RNA as extracted at the selected time period to the multiplex analyzer and determining RNA concentrations at the plurality of selected time periods includes an apparatus configured to directly detect messenger RNA (mRNA) molecules of interest using target specific, color-coded probe pairs.

Aspect 13. The method of any of aspects 1-12, wherein the at least one targeted microbe is a pathogen.

Aspect 14. A method, comprising: anaerobically reconstituting a first sample of a target microbe to produce a reconstituted target microbe; anaerobically reconstituting a community of microbes including a second sample of the target microbe to produce a reconstituted microbial community; extracting ribonucleic acid (RNA) from the reconstituted target microbe at a plurality of selected time periods after reconstitution; extracting RNA from the reconstituted microbial community at the plurality of selected time periods after reconstitution; subjecting the RNA from the reconstituted target microbe at the plurality of selected time periods to a multiplex analyzer and determining RNA concentrations at the plurality of selected time periods; subjecting the RNA extracted from the reconstituted microbial community at the plurality of selected time periods to the multiplex analyzer and determining RNA concentrations at the plurality of selected time periods; comparing the RNA concentration of the reconstituted target microbe with the RNA concentration of the target microbe in the reconstituted microbial community; wherein a lower RNA concentration of the reconstituted target microbe, relative to the RNA concentration of the target microbe in the reconstituted microbial community, indicates that the metabolic activity of the target microbe is enhanced by the community of microbes; and wherein a higher RNA concentration of the reconstituted target microbe, relative to the RNA concentration of the target microbe in the reconstituted microbial community, indicates that the metabolic activity of the target microbe is inhibited by the community of microbes.

Aspect 15. The method of aspect 14, wherein the plurality of selected time periods are between and including 0 minutes and 2 hours.

Aspect 16. The method of one of aspects 14 or 15, wherein the plurality of selected time periods include 0 minutes, 10 minutes, 30 minutes, and 1 hour.

Aspect 17. The method of any of aspects 14-16, comprising: lyophilizing the target microbe prior to the reconstituting; and lyophilizing the community of microbes prior to the reconstituting.

Aspect 18. The method of any of aspects 14-17, comprising: freezing the target microbe and the community of microbes prior to the reconstituting.

Aspect 19. The method of any of aspects 14-18, wherein the multiplex analyzer includes a NanoString® RNA Assay.

Aspect 20. The method of any of aspects 14-19, wherein the targeted microbe is a strain included in one or more of MET-1, MET-2, MET-3, or MET-4 as defined above.

Aspect 21. The method of any of aspects 14-20, wherein subjecting the RNA as extracted at the selected time period to the multiplex analyzer and determining RNA concentrations at the plurality of selected time periods includes detecting RNA without reverse transcription.

Aspect 22. The method of aspect 21, wherein subjecting the RNA as extracted at the selected time period to the multiplex analyzer and determining RNA concentrations at the plurality of selected time periods includes counting RNA without detecting complementary deoxyribonucleic acid (cDNA) as a proxy of the RNA.

Aspect 23. The method of aspect 21, wherein subjecting the RNA as extracted at the selected time period to the multiplex analyzer and determining RNA concentrations at the plurality of selected time periods includes an apparatus configured to directly detect messenger RNA (mRNA) molecules of interest using target specific, color-coded probe pairs.

Aspect 24. The method of any of aspects 14-23, wherein the plurality of selected time periods in the extracting ribonucleic acid (RNA) from the reconstituted target microbe and the extracting RNA from the reconstituted microbial community are the same.

Aspect 25. A method for designing a microbe community that is stable and includes a plurality of microbes working together, comprising any of aspects 1-24.

Aspect 26. A method for detecting living microbes in a microbial mixture after lyophilization, comprising any of aspects 1-13.

Aspect 27. A method for determining the interactions of a target microbe with a community of microbes containing the target microbe, comprising any of aspects 14-23.

Aspect 28. A treatment method, comprising: determining a microbial community of a patient; identifying a target microbial community for the patient; and tailoring a Microbial Ecosystem Therapeutic (MET) to achieve the target microbial community for the patient.

Aspect 29. The treatment method of aspect 28, comprising administering the MET to the patient.

Aspect 30. The treatment method of one of aspects 28 or 29, wherein the tailoring comprises the method of any of aspects 1-24.

Aspect 31. A Microbial Ecosystem Therapeutic (MET), comprising: a microbial community including a plurality of microbes, wherein the microbial community is prepared using the method according to any of aspects 1-24.

Aspect 32. A method, comprising: determining a microbial community of a patient; identifying a target microbial community for the patient; and tailoring a Microbial Ecosystem Therapeutic (MET) to achieve the target microbial community for the patient.

Aspect 33. The method of aspect 32, comprising administering the MET to the patient.

Aspect 34. The method of one of aspects 32 or 33, wherein the tailoring comprises the method of any of aspects 1-24.

Aspect 35. A Microbial Ecosystem Therapeutic (MET), tailored to achieve a target microbial community for a patient for use in a method of treatment of a disorder of the patient.

Aspect 36. The MET of aspect 35, wherein the disorder of the patient comprises one or more of gastrointestinal disorders, metabolic syndromes, psychological disorders (e.g., depression and anxiety), cancer, inflammatory disorders, autoimmune disorders, and central nervous system disorders.

Aspect 37. The MET of one of aspects 35 or 36, comprising: a microbial community including a plurality of microbes, wherein the microbial community is prepared using the method according to any of aspects 1-24.

Among those benefits and improvements that have been disclosed, other objects and advantages will become apparent from the preceding description in conjunction with the accompanying figures. Detailed embodiments are disclosed. The disclosed embodiments are merely illustrative and may be embodied in various forms. In addition, each of the examples given in connection with the various embodiments are intended to be illustrative, and not restrictive. It is to be understood that changes may be made in detail, especially in matters of the construction materials employed and the shape, size, and arrangement of parts without departing from the scope of the present disclosure. This Specification and the embodiments described are examples, with the true scope and spirit of the disclosure being indicated by the claims that follow.

The terminology used herein is intended to describe embodiments and is not intended to be limiting. The terms "a," "an," and "the" include the plural forms as well, unless clearly indicated otherwise. The terms "comprises" and/or "comprising," when used in this Specification, specify the presence of the stated features, integers, steps, operations, elements, and/or components, but do not preclude the presence or addition of one or more other features, integers, steps, operations, elements, and/or components.

What is claimed is:

1. A method, comprising:
reconstituting a lyophilized microbial community;
extracting ribonucleic acid (RNA) of metabolically associated genes from at least one targeted microbe in the reconstituted microbial community at a plurality of selected time periods;
subjecting the RNA of metabolically associated genes as extracted at the selected time period to a multiplex analyzer and determining RNA concentrations of metabolically associated genes at the plurality of selected time periods;
wherein an increase in the RNA concentration from a first of the plurality of selected time periods to a second of the plurality of time periods indicates RNA expression of metabolically associated genes from the at least one targeted microbe; and
wherein RNA expression of metabolically associated genes from the at least one targeted microbe indicates that the at least one targeted microbe is a living microbe.

2. The method of claim 1, wherein the plurality of selected time periods are between and including 0 minutes and 2 hours.

3. The method of claim 1, wherein the plurality of selected time periods include 0 minutes, 10 minutes, 30 minutes, and 1 hour after the at least one targeted microbe is reconstituted.

4. The method of claim 3, wherein an increase in RNA concentration is determined between and including 0 minutes and at least one of 10 minutes, 20 minutes, 30 minutes, 1 hour, or 2 hours.

5. The method of claim 1, comprising:
lyophilizing the microbial community prior to the reconstituting.

6. The method of claim 1, wherein the reconstituting includes anaerobically reconstituting the lyophilized microbial community.

7. The method of claim 1, wherein subjecting the RNA as extracted at the selected time period to the multiplex analyzer and determining RNA concentrations at the plurality of selected time periods includes detecting RNA without reverse transcription.

8. The method of claim 7, wherein subjecting the RNA as extracted at the selected time period to the multiplex analyzer and determining RNA concentrations at the plurality of selected time periods includes counting RNA without detecting complementary deoxyribonucleic acid (cDNA) as a proxy of the RNA.

9. The method of claim 7, wherein subjecting the RNA as extracted at the selected time period to the multiplex analyzer and determining RNA concentrations at the plurality of selected time periods includes an apparatus configured to directly detect messenger RNA (mRNA) molecules of interest using target specific, color-coded probe pairs.

10. The method of claim 1, wherein the at least one targeted microbe is a pathogen.

11. A method, comprising:
anaerobically reconstituting a first sample of a target microbe to produce a reconstituted target microbe;
anaerobically reconstituting a community of microbes including a second sample of the target microbe to produce a reconstituted microbial community;

extracting ribonucleic acid (RNA) of metabolically associated genes from the reconstituted target microbe at a plurality of selected time periods after reconstitution;

extracting RNA of metabolically associated genes from the reconstituted microbial community at the plurality of selected time periods after reconstitution;

subjecting the RNA of metabolically associated genes from the reconstituted target microbe at the plurality of selected time periods to a multiplex analyzer and determining RNA concentrations of metabolically associated genes at the plurality of selected time periods;

subjecting the RNA of metabolically associated genes extracted from the reconstituted microbial community at the plurality of selected time periods to the multiplex analyzer and determining RNA concentrations of metabolically associated genes at the plurality of selected time periods;

comparing the RNA concentration of metabolically associated genes of the reconstituted target microbe with the RNA concentration of metabolically associated genes of the target microbe in the reconstituted microbial community;

wherein a lower RNA concentration of metabolically associated genes of the reconstituted target microbe, relative to the RNA concentration of metabolically associated genes of the target microbe in the reconstituted microbial community, indicates that the metabolic activity of the target microbe is enhanced by the community of microbes; and wherein a higher RNA concentration of the reconstituted target microbe, relative to the RNA concentration of the target microbe in the reconstituted microbial community, indicates that the metabolic activity of the target microbe is inhibited by the community of microbes.

12. The method of claim 11, wherein the plurality of selected time periods are between and including 0 minutes and 2 hours.

13. The method of claim 11, wherein the plurality of selected time periods include 0 minutes, 10 minutes, 30 minutes, and 1 hour.

14. The method of claim 11, comprising:
lyophilizing the target microbe prior to the reconstituting; and
lyophilizing the community of microbes prior to the reconstituting.

15. The method of claim 11, wherein subjecting the RNA as extracted at the selected time period to the multiplex analyzer and determining RNA concentrations at the plurality of selected time periods includes detecting RNA without reverse transcription.

16. The method of claim 15, wherein subjecting the RNA as extracted at the selected time period to the multiplex analyzer and determining RNA concentrations at the plurality of selected time periods includes counting RNA without detecting complementary deoxyribonucleic acid (cDNA) as a proxy of the RNA.

17. The method of claim 15, wherein subjecting the RNA as extracted at the selected time period to the multiplex analyzer and determining RNA concentrations at the plurality of selected time periods includes an apparatus configured to directly detect messenger RNA (mRNA) molecules of interest using target specific, color-coded probe pairs.

18. The method of claim 11, wherein the plurality of selected time periods in the extracting ribonucleic acid (RNA) from the reconstituted target microbe and the extracting RNA from the reconstituted microbial community are the same.

* * * * *